Figure 2B:
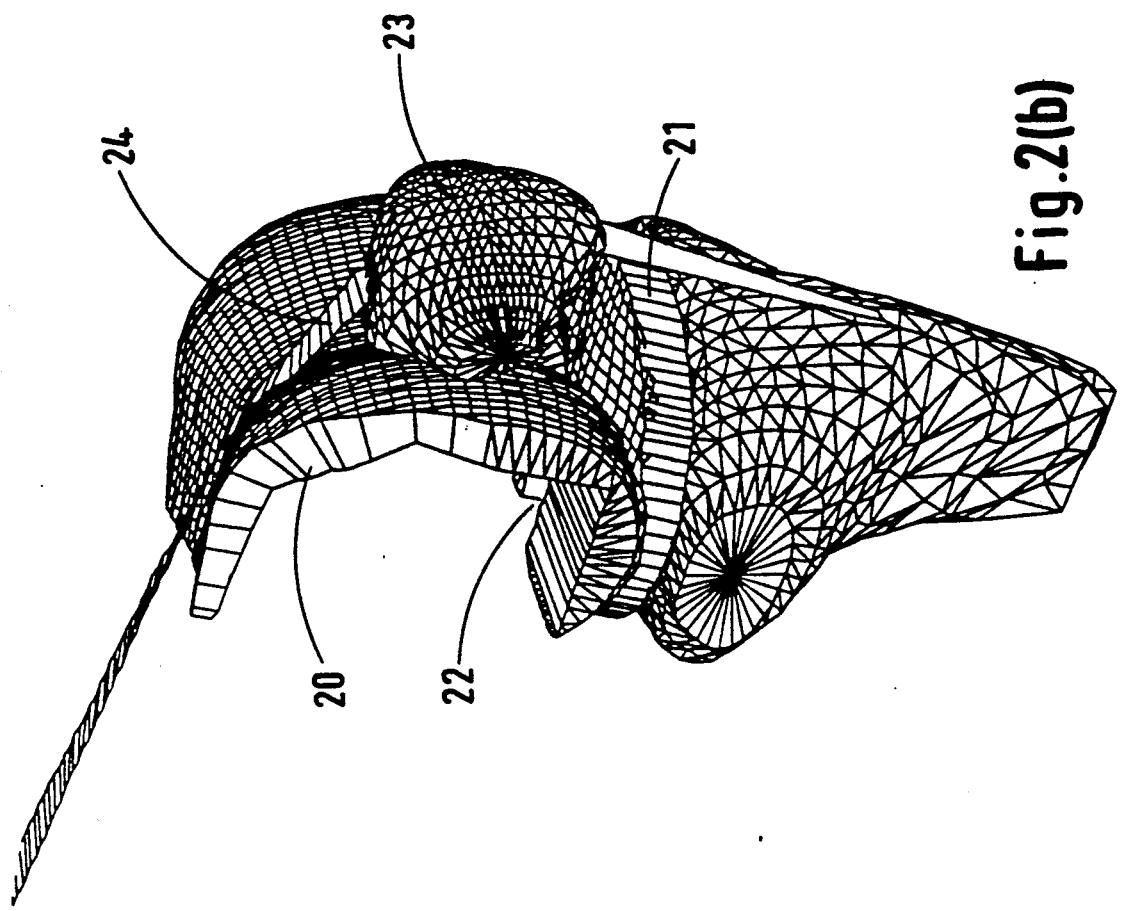

United States Patent [19]

Walker

[11] Patent Number: 5,330,533
[45] Date of Patent: Jul. 19, 1994

[54] PROSTHESIS FOR KNEE REPLACEMENT

[76] Inventor: Peter S. Walker, The Institute of Orthopaedics, Department of Biomedical Engineering, Royal National Orthopaedic Hospital, Brockley Hill, Stanmore, Middlesex H47 4LP, England

[21] Appl. No.: 829,369

[22] Filed: Feb. 3, 1992

[30] Foreign Application Priority Data

Feb. 4, 1991 [GB] United Kingdom ............ 91 02348.1

[51] Int. Cl.$^5$ ................................................ A61F 2/38
[52] U.S. Cl. ........................................................ 623/20
[58] Field of Search .............................. 623/20, 16, 18

[56] References Cited

U.S. PATENT DOCUMENTS

| | | | |
|---|---|---|---|
| 3,958,278 | 5/1976 | Lee et al. | 623/20 |
| 4,085,466 | 4/1978 | Goodfellow et al. | |
| 4,215,439 | 8/1980 | Gold et al. | 623/20 |
| 4,224,696 | 9/1980 | Murray et al. | |
| 4,340,978 | 7/1982 | Buechel et al. | |
| 4,586,933 | 5/1986 | Shoji et al. | 623/20 |
| 4,673,407 | 6/1987 | Martin | 623/20 |
| 4,711,639 | 12/1987 | Grundei | 623/20 |
| 4,714,474 | 12/1987 | Brooks, Jr. et al. | 623/20 |
| 4,822,362 | 4/1989 | Walker et al. | 623/20 |
| 4,822,365 | 4/1989 | Walker et al. | |
| 5,064,437 | 11/1991 | Stock et al. | 623/20 |
| 5,080,675 | 1/1992 | Lawes et al. | 623/20 |
| 5,116,375 | 5/1992 | Hofmann | 623/20 |
| 5,133,758 | 7/1992 | Hollister | 623/20 |
| 5,147,405 | 9/1992 | Van Zile et al. | 623/20 |
| 5,219,362 | 6/1993 | Tuke et al. | 623/20 |

FOREIGN PATENT DOCUMENTS

| | | | |
|---|---|---|---|
| 0349173 | 6/1989 | European Pat. Off. | |
| 0442330 | 2/1991 | European Pat. Off. | 623/20 |
| 3529894 | 3/1987 | Fed. Rep. of Germany | 623/20 |
| 4009360 | 8/1991 | Fed. Rep. of Germany | |
| 2219942 | 12/1989 | United Kingdom | 623/20 |

Primary Examiner—Randall L. Green
Assistant Examiner—Mary Beth Jones
Attorney, Agent, or Firm—Lowe, Price, LeBlanc & Becker

[57] ABSTRACT

A knee prosthesis includes a femoral component in which the condyles have a continuous contact surface for the tibial bearing surface and in which the sagittal radius is constant from posterior to a point more anterior than the distalmost point. The tibial bearing surface is shaped to have a curvature which corresponds closely with that of the femoral condylar surfaces. The tibial component includes a plastics meniscus component supported on a metal platform for sliding movement in the anterior-posterior direction and the mating surface between the meniscus and platform has a sagittal curvature which is larger than the sagittal radius of the femoral condyles.

17 Claims, 7 Drawing Sheets

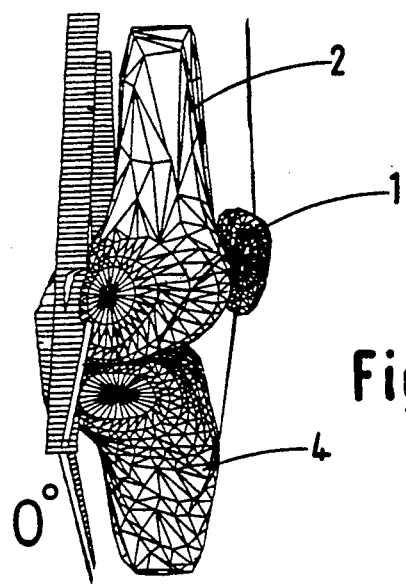
Fig.1(a) 0°
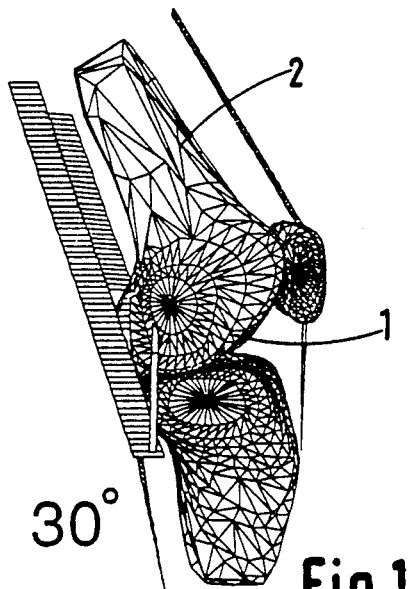
Fig.1(b) 30°
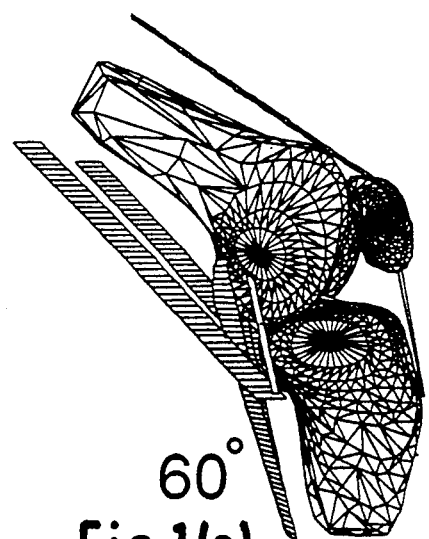
Fig.1(c) 60°
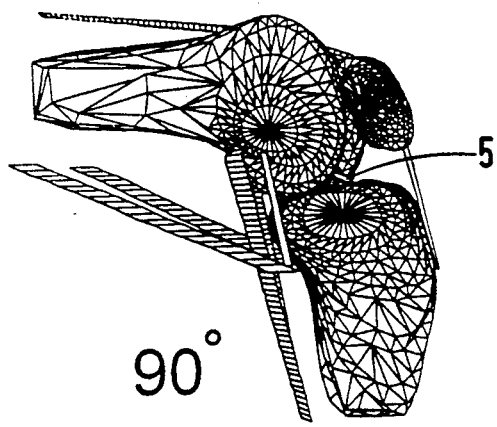
Fig.1(d) 90°
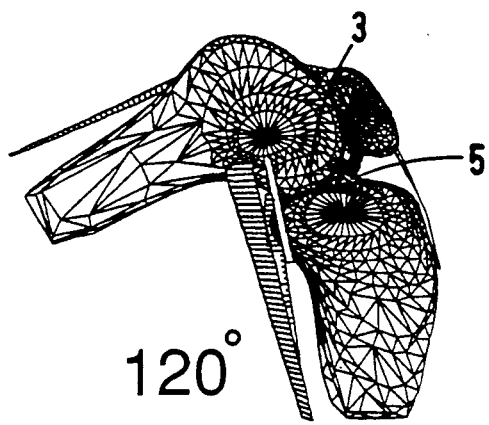
Fig.1(e) 120°

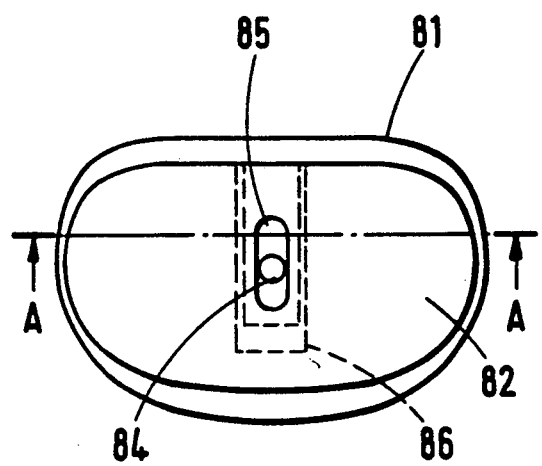
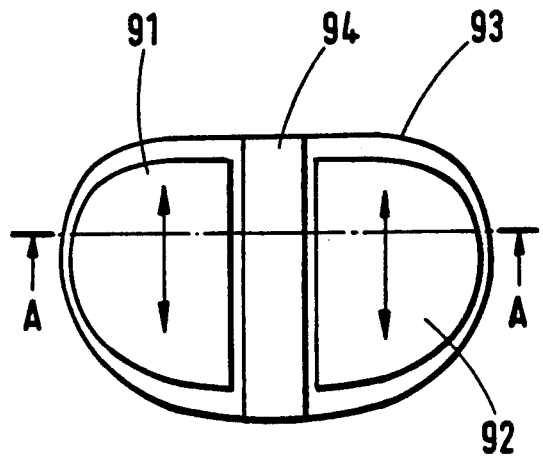
Fig.8(a)
Fig.9(a)
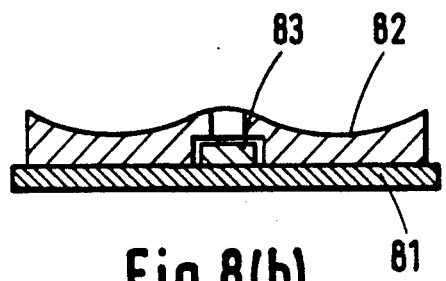
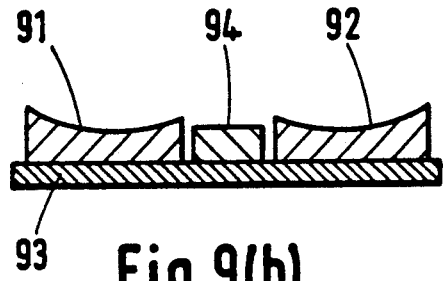
Fig.8(b)
Fig.9(b)
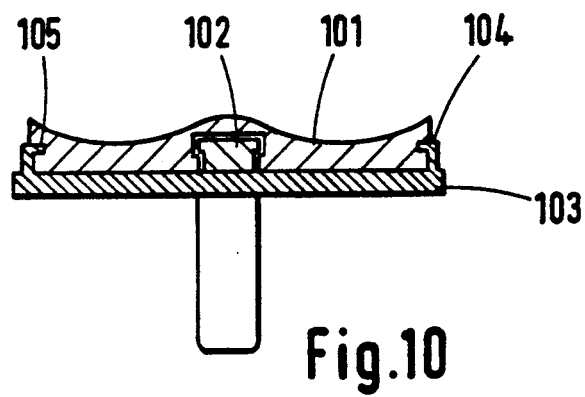
Fig.10

PROSTHESIS FOR KNEE REPLACEMENT

This invention relates to prostheses for knee replacement.

BACKGROUND OF THE INVENTION

Most of the knee replacement designs in current use are of the Condylar Replacement type, where the arthritic joint surfaces are resected and are replaced with metal and plastic surfaces. There are two conflicting requirements in design; first, the desirability for freedom of motion requires relatively low conformity between the femoral and tibial surfaces, while the desirability for low contact stresses on the plastic surface requires high conformity. This conflict similarly applies to the patello-femoral bearing joint.

SUMMARY OF THE INVENTION

The present invention provides two approaches to a solution of this dilemma. First, it provides a femoral component which alters the sagittal radius and which has continuous contact surfaces for the tibial surface and also, preferably, with the patella surface. Secondly, the invention relates to a sliding bearing type of prosthesis where guide tracks for the tibial bearing surface are curved in the sagittal plane to provide the necessary stability, as well as freedom for translational motion in the anterior-posterior direction.

The above two broad concepts may be combined in a single prosthesis or employed individually depending on the requirements of a particular case. The invention also includes variations of the above concepts and various designs of tibial components.

According to one aspect of the invention there is provided a knee prosthesis which comprises a femoral component having a bearing surface whose radius in each sagittal section, over a substantial distance in the lateral-medial direction, is substantially constant from posterior to a point more anterior than the distalmost point, and a tibial component having a concave bearing surface for supporting the femoral component, the bearing surfaces in the respective sagittal sections of the femoral and tibial components being substantially continuous from posterior to anterior whereby contact between the femoral and tibial surfaces can be maintained across a substantial width of the joint throughout the range of flexion.

Preferably, the tibial bearing surface, when viewed in one or more sagittal sections, has a radius of curvature which substantially corresponds with the radius of the bearing surface of the femoral component. However, there may be differences in the profiles of the sagittal sections, provided that contact is substantially continuous from posterior to anterior. Indeed, this is desirable to provide for the required laxity in the joint. For example, the radii of the femoral sagittal sections may be slightly smaller than the radii of the corresponding sections of the tibial bearing surface, so as to allow sufficient clearance for taking up differences in surgical placement of the two components of the prosthesis, and allowing adequate laxity for normal functions.

Where the cruciate ligaments are retained in the fitting of the prosthesis, the femoral component portion which encases the resected condyles may be formed with a slot to permit passage of the ligaments. However, many surgeons prefer to resect the cruciate ligaments and in this case, the femoral component may be continued in the distal/posterior region across the full width, i.e in the lateral-medial direction.

The extent to which the constant radius of the femoral component in sagittal planes extends around the distalmost point is the amount sufficient to give the desired degree of flexion of the joint.

Preferably, the anterior face of the femoral component is formed with a patella groove which is shaped so that there is contact between the patella and the groove through all degrees of flexion.

Conformity of the femoral and tibial bearing surfaces during all stages of flexion gives increased contact area between the metal and plastic bearing surfaces, leading to reduced wear and deformation. Also, as the sagittal curvature of the tibial component is upwardly concave, the up-sweep of the tibial bearing surface posteriorly and anteriorly gives increased stability in anterior-posterior, medial-lateral and internal-external rotations. Close contact between the patella (whether natural or artificial) with the patella groove during all stages of flexion also contributes to greater stability of the joint.

According to a second aspect of the invention there is provided a tibial component of a knee prosthesis which comprises a metal platform adapted to be secured to a resected tibia and a plastics bearing component mounted for sliding movement thereon, the mating surface between the plastics component and the metal platform being substantially cylindrical with the axis of the cylinder extending in a lateral-medial line and the radius of the cylinder being larger than the maximum sagittal radius of the bearing surface between the femoral and tibial components. The curvature of the bearing surface between the femoral component and the tibial component in the sagittal plane is in the same sense as the curvature of the cylindrical mating surface, between the plastics component and the metal platform.

By providing for sliding movement in the anterior-posterior direction, the prosthesis has freedom of movement in the anterior-posterior direction, which allows a higher degree of flexion, while reducing shear stresses in the component-bone interfaces.

The cylindrical bearing surface between the plastics component and the metal platform viewed in a sagittal plane constrains the movement in the anterior-posterior direction. Also, the upwardly curved interface between the plastics component and the metal platform introduces increasing constraint due to gravity forces as the plastics bearing component displaces further away from its central position.

Figure 2A:
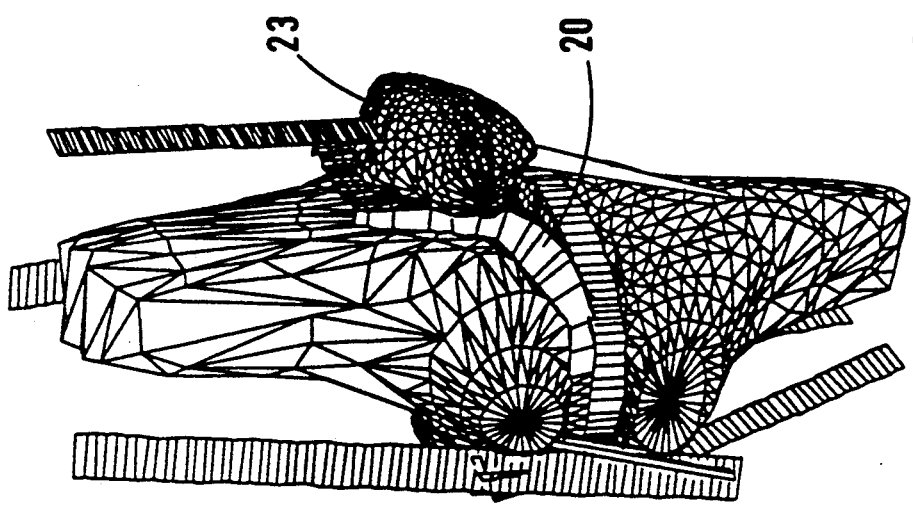
Figure 3A:
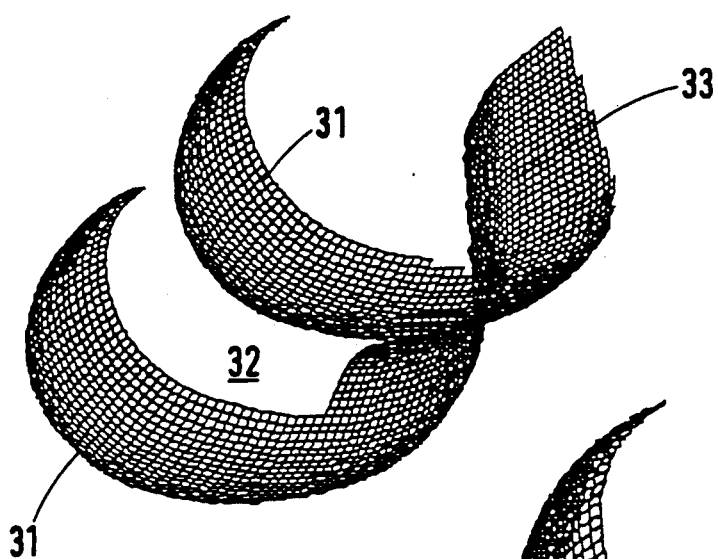
Figure 3B:
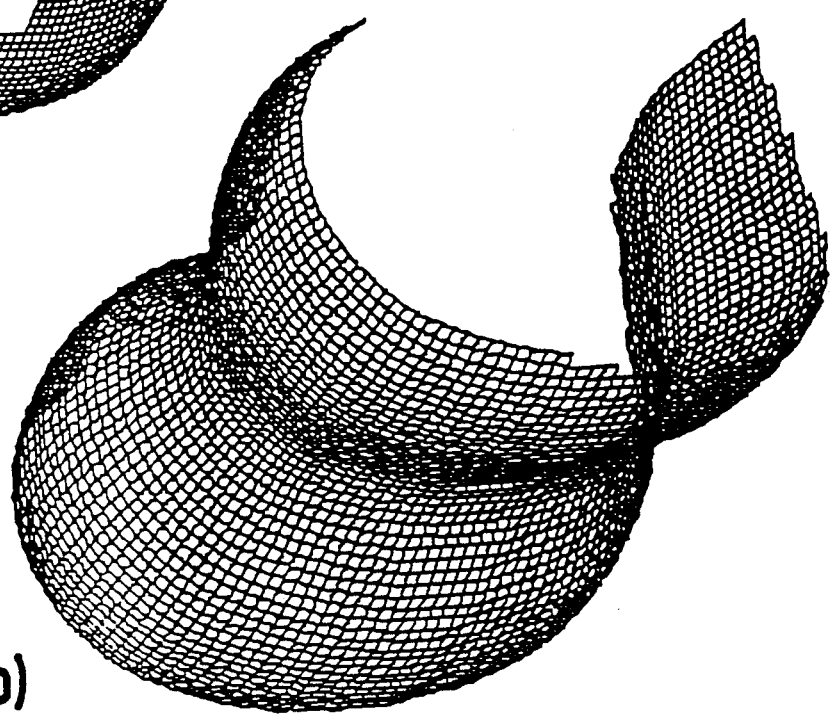
Figure 3C:
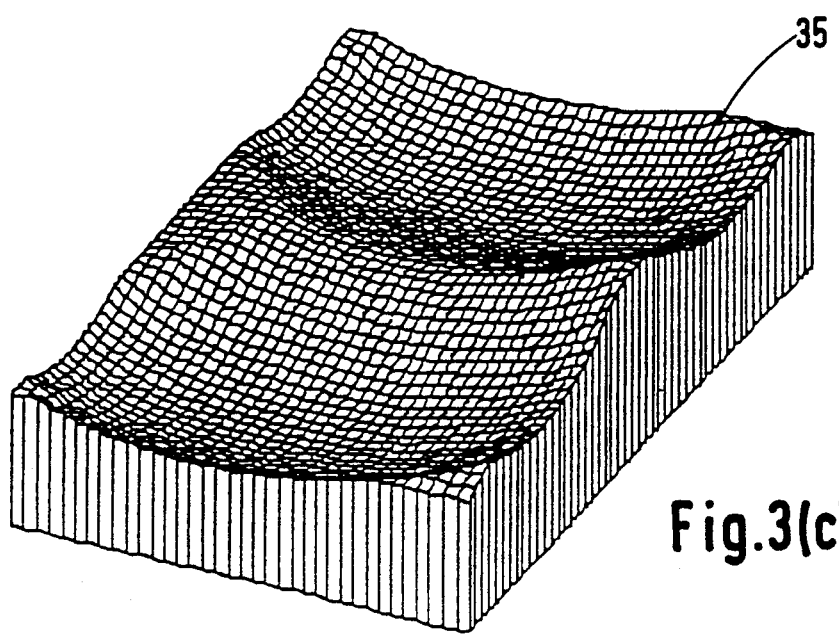
Figure 4A:
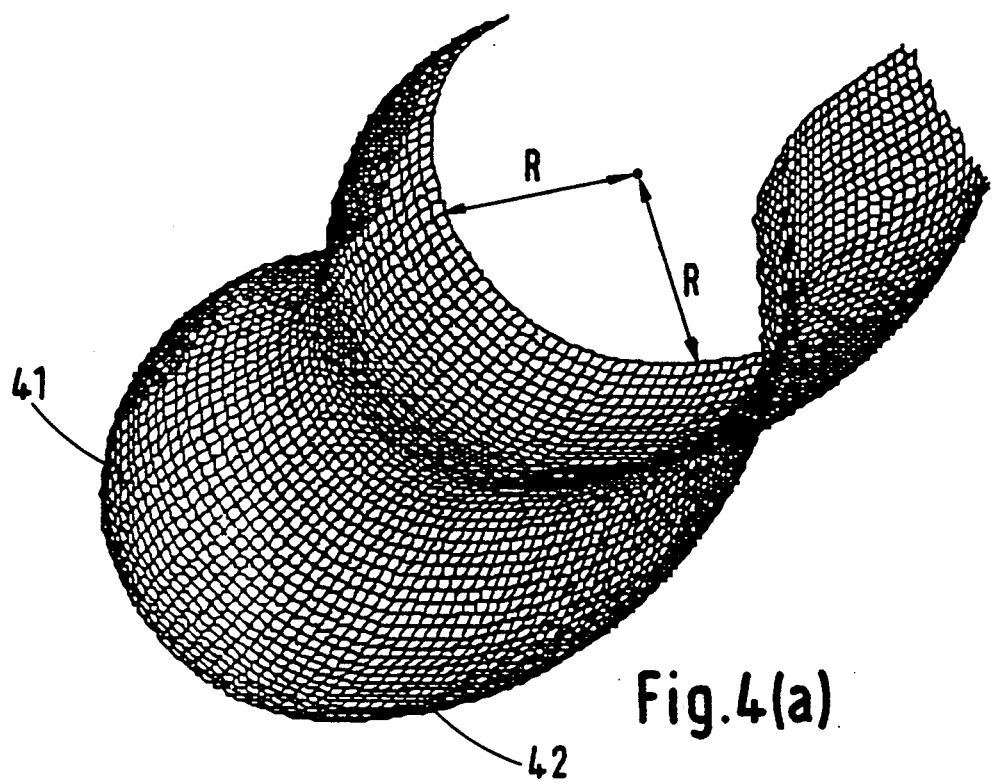
Figure 4B:
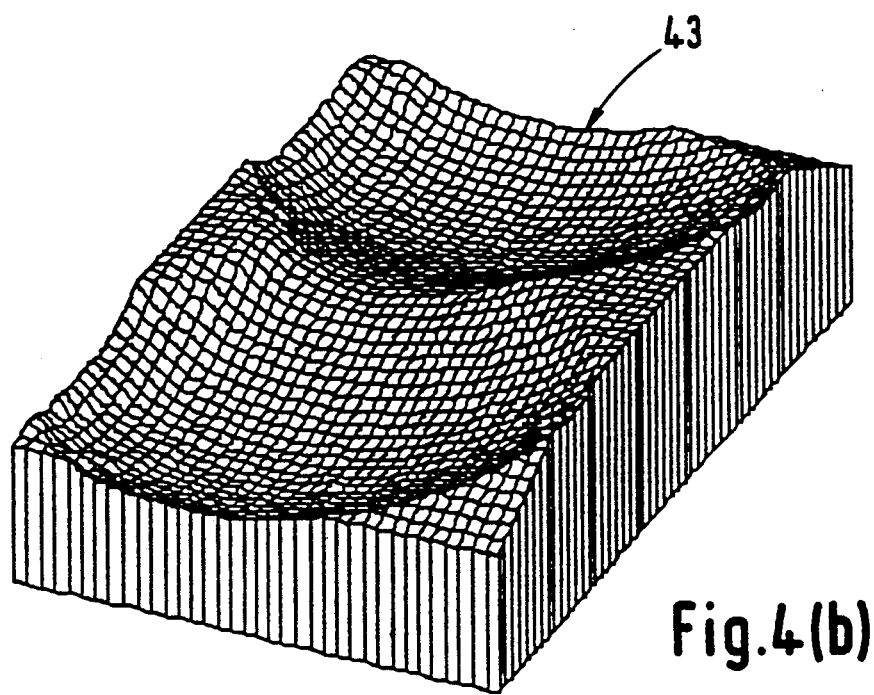
Figure 5D:
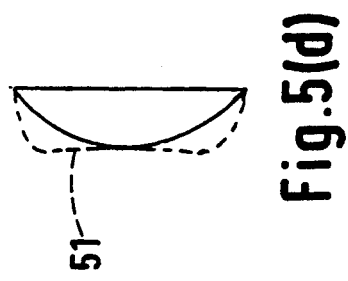
Figure 5C:
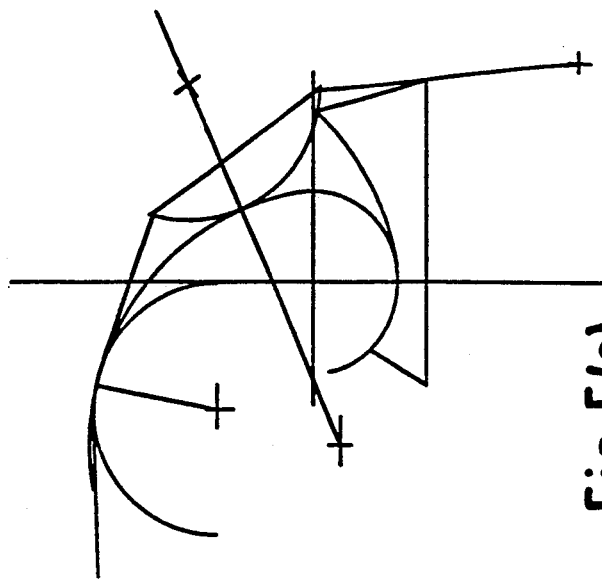
Figure 5B:
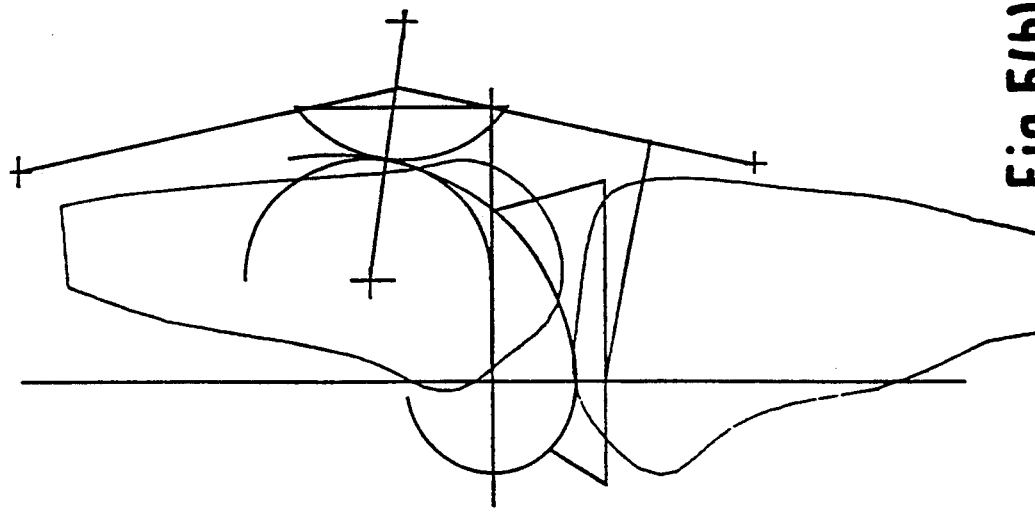
Figure 5A:
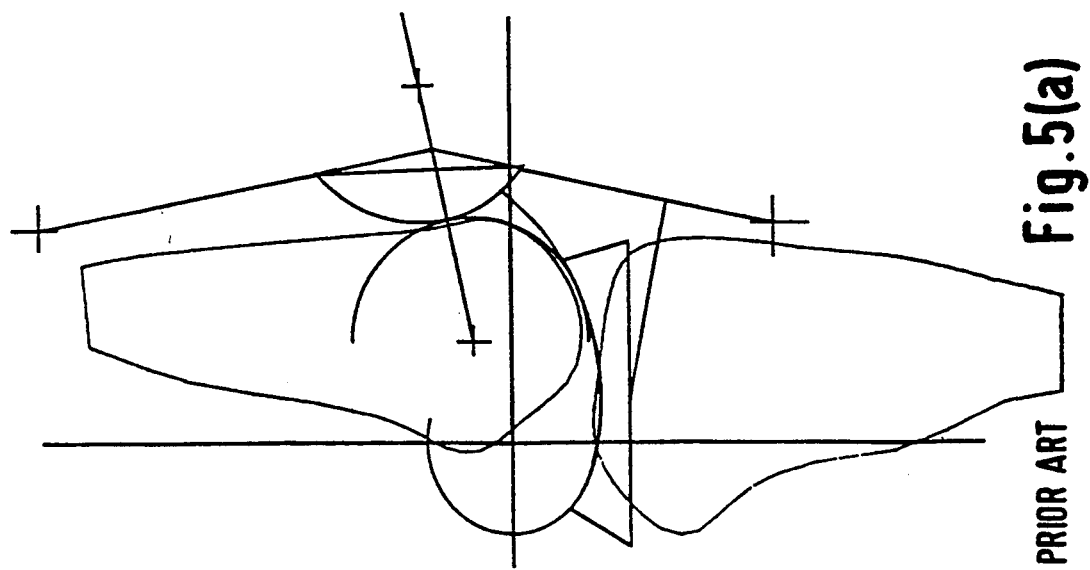
Figure 6:
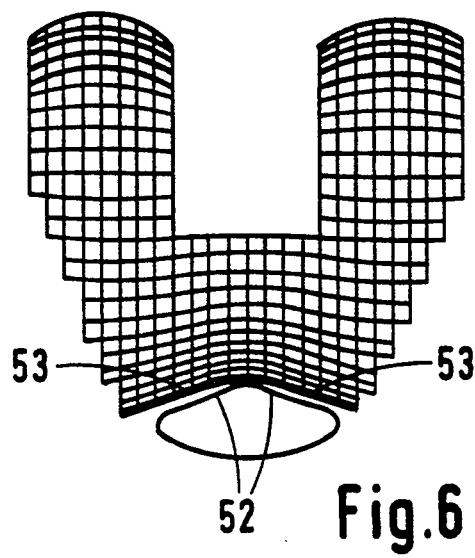
Figure 7A:
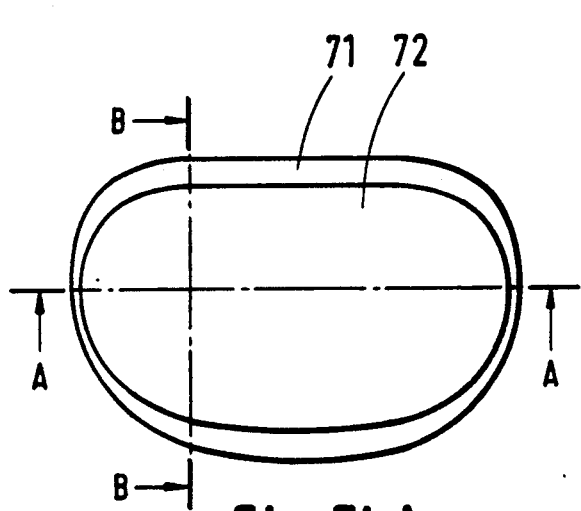
Figure 7B:
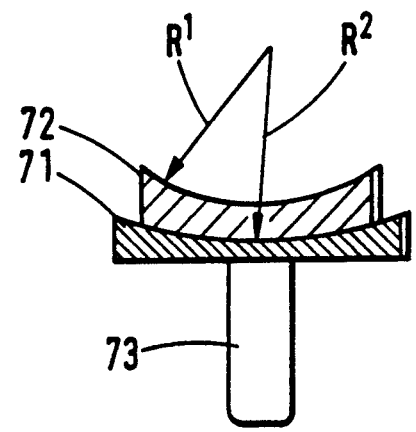
Figure 7C:
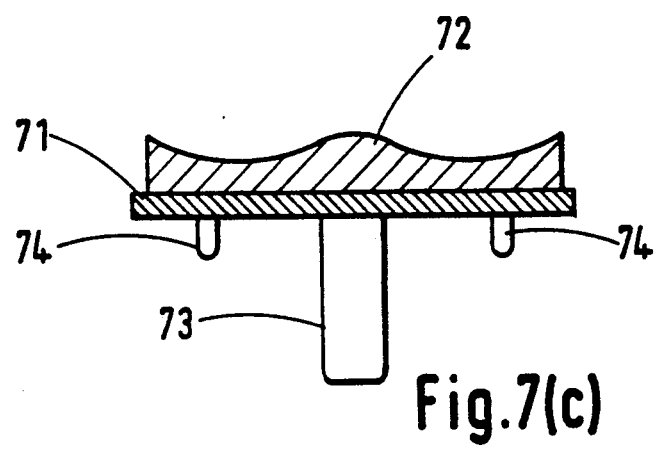

Various features and advantages of the present invention will become clear from the following description and accompanying drawings in which:

FIGS. 1(a), (b), (c), (d) and (e) are perspective views of the normal knee at various degrees of flexion from 0° to 120°, FIG. 2(a) is a perspective view of a knee fitted with a prosthesis in accordance with the invention at zero flexion, FIG. 2(b) is a perspective view of the knee (with the femur removed for clarity), fitted with same prosthesis at approximately 90° flexion, FIG. 3(a) is a perspective view of a femoral component in accordance with a first embodiment of the invention, FIG. 3(b) is a view similar to FIG. 3(a) of a modified form of the femoral component, FIG. 3(c) is a perspective view of a tibial component intended for use with the femoral component of FIG. 3(b), FIG. 4(a) is a perspective view similar to FIG. 3(a) of a further embodiment in accordance with the invention and FIG. 4(b) shows a perspective view of a corresponding tibial component, FIGS. 5(a), (b) & (c) show, diagrammatically, sagittal views of a prosthesis in accordance with the invention (FIGS. 5(b) & (c)) compared with a conventional design (FIG. 5(a)), FIG. 5(d) is a sagittal view of the profile of a patella replacement (in broken lines) compared with a conventional replacement (full lines), FIG. 6 is an underside view of a femoral component showing the conformity of the patella with the patella groove, FIG. 7(a) is a plan view of a tibial component in accordance with the invention, FIG. 7(b) is a section taken on the line B—B in FIG. 7(a), FIG. 7(c) is a section taken on the line A—A in FIG. 7(a), FIG. 8(a) is a plan view of a modified tibial component, FIG. 8(b) is a section taken on the line A—A in FIG. 8(a) but with the anchoring pegs omitted, FIG. 9(a) is a plan view of a further embodiment of tibial component and FIG. 9(b) is a view taken on the line A—A in FIG. 9(a), and FIG. 10 is a view similar to FIGS. 7(b), 8(b) and 9b) of a modified tibial component showing alternative ways of guiding the plastics component.

FIG. 1 of the accompanying drawings shows a sagittal view of the natural knee at different flexion angles —0 to 120° in thirty degree steps. The distal end 1 of the femur 2 can be seen to have a larger radius than the posterior 3. At zero degrees flexion, the larger radius distal end 1 contacts the top of the tibia 4, resulting in greater conformity and a greater area of contact. Other structures increase the contact area, notably the menisci, which are deformable discs interposed between the femoral and tibial condyles. When the knee is flexed, the femoral-tibial conformity is reduced, which would reduce the contact area and result in high contact stresses. However, the deformable menisci take up the shape between the femoral and tibial surface and once again spread the load. if the menisci are removed for injury, in later years, there is an increased chance of osteroarthritis.

The knee displays both laxity (which can be termed freedom of motion) and stability, which is the control of displacements and rotations to within acceptable limits. Laxity can include linear or rotational translation in any of the three mutually perpendicular coordinate axes. For purposes of the invention, laxity is only considered in anterior-posterior displacement, medial-lateral displacement and internal-external rotation, these being the most significant. The anterior-posterior stability is provided mainly by the cruciate ligaments. The anterior cruciate 5 can be seen in FIG. 1, especially at the higher flexion angles. Rotational stability is provided by a combination of the cruciate and collateral ligaments. The muscles also play an important role in providing stability. The joint surfaces contribute to stability as force is applied across the joint, due to the slight dishing of the surfaces and the deformability of the articular cartilage. The laxity is due to the elastic extensibility of the ligaments, the joint surfaces, and other soft tissues surrounding the joint.

The patella is an important bone which transmits the force between the quadriceps and the upper tibia. In broad terms it can be regarded as a pulley, sliding up and down on the front of the femur. The patella fits closely into a groove on the front of the femur, such that the contact areas are broad bands across the width of the patella. Beyond about 90 degrees of flexion, the contact splits into two parts as the patella straddles the intercondylar groove.

When a condylar replacement is introduced (FIG. 2), a femoral component 20 is attached to the end of the femur and a tibial component 21 to the upper part of the tibia. Normally, the ends of the femoral condyles are resacted and shaped to receive the femoral component and held in place with bone cement and/or pegs extending into the condyles. The collateral and cruciate ligaments can be preserved by providing a slot 22 in the femoral component, although in most designs, either the anterior is resected, or both cruciates are resected. The patella 23, either the natural patella or a replacement, fits into the groove 24. When the knee is flexed with conventional prostheses, there is now a distinct lack of conformity between the femoral and tibial surfaces, with the result that the contact stresses on the plastic surface are high, leading to failure due to breakdown of the plastic in many cases.

Prior designs suffer from a number of problems; for example there is no meniscus to spread the force as in the normal knee. If the anterior cruciate is resacted, there should ideally be a posterior upsweep of the tibial plastic surface to compensate, and if the posterior cruciate is resected also, an anterior upsweep is needed. In angles of flexion beyond about 90 degrees, there are two separate contacts on the patella component, leading to high stresses and deformation, and also sometimes 'catching'.

A typical femoral component in accordance with the invention is shown in FIG. 3(a). The condylar surfaces 31 resemble the anatomical, especially in the sagittal view, and there is a cut-out or slot 32 for one or both cruciate ligaments. A patella groove 33 is continuous down to the cut-out 32 after which it splits. The larger femoral component in FIG. 3(b) now has continuous surfaces throughout, including the patella groove, but is otherwise the same. Such a configuration requires resection of both cruciate ligaments. The femoral shape is then used to computer-generate a tibial surface 35, based on input laxity requirements in anterior-posterior displacement and internal-external rotation. A computerized method of generating tibial surfaces is described in U.S. Pat. No. 4,822,365. The new femoral shape has two advantages. First, the contact on the tibial surface can now be spread over the entire width of the tibial surface, thus increasing the contact area. Second, the patella has a continuous track, and can maintain a broad contact area throughout motion, without a split of the contacts at higher flexion. However, there is still the disadvantage that the radius of curvature of the distal femur is greater than the posterior, such that once flexion is initiated, the smaller femoral radius contacts the tibia giving a reduction in contact area.

FIGS. 4(a) and 4(b) shows one solution to this problem. Here, the radius of the posterior portion 41 of the femoral component has been carried round to the distal femur 42. Now there is a constant radius R for contacting the tibial surface 43. A surface computer-generated with this component is clearly more dished than the previous component and provides an increase in the contact area throughout. The reduction in the contact stresses are calculated to be significant. Another benefit of the new surfaces is the enhanced stability. In the surfaces of FIG. 3, it can be imagined that the flexed femur can slide forwards on the tibia with relatively little resistance. However, in FIG. 4, the anterior sliding is much more restricted because of the steeper slope of the anterior tibial surface.

Certain characteristics of this design form are illustrated in FIG. 5 which shows sagittal views of a standard design (FIG. 5(a)) and a design in accordance with the invention, (FIGS. 5(b) and 5(c)). The differences in the distal femoral radii can be clearly seen. This change in distal radius has three consequences. More resection of anterior bone is needed for installation, although this is not a serious problem. The second problem is that the patella mechanics are altered. An important parameter of patella function is the lever arm, because this helps to determine quadriceps efficiency. With the knee at zero flexion, the lever arms are similar, but in mid-flexion (around 45 degrees), it can be appreciated that the lever arm of the design on the right will be reduced. This may not be a serious problem, but a possible remedy is to treat the bearing surfaces and patella surfaces as separate. The patella surface would then protrude as normal, in between the bearing surfaces. Such a solution reduces the width of the main bearing areas and may not represent an overall advantage. A final characteristic is that the femoral-tibial contact point is more posterior than normal. This has the advantage of improved quadriceps efficiency, as noted, but may result in upwards tilting of the front of the tibial component. If necessary, the position of the bottom of the curvature on the tibial surface could be moved anteriorly by 2-3 mm which would alleviate this problem.

An improvement to the patello-femoral contact is apparent from FIG. 5. The normal dome-shape (FIG. 5(a)) has high conformity when seen in the overhead view (FIG. 6), but low conformity in the sagittal view. Several experimental and theoretical studies has shown that the angle through which the patella rotates relative to the femoral component in the sagittal plane is within 10 degrees (FIG. 5(b) and 5(c)). This means that a high degree of conformity can be designed into the patella with no loss in freedom of motion. The new sagittal profile of the patella is shown dotted in FIG. 5(d). As can be seen, instead of having a continuous convex shape in sagittal view, it has a flattened inner face 51 and outwardly extending surfaces 52 (FIG. 6), giving greater conformity with the sides of the patella groove 53. Such increase in conformity leads to greatly reduced contact stresses. A consequence of such a design is that if surgical placement is rotationally incorrect, there would be restriction of motion. However, the curvatures can be adjusted to allow for an appropriate margin of error.

The above design form in accordance with the invention is most suitable when the anterior and posterior cruciate ligaments are resected. In this case, there will still be sufficient anterior-posterior laxity (approximately 5 mm total) and rotational laxity ($+-12$ degrees), without restriction from taut ligaments. Such laxity will also be sufficient for activities of everyday living. The disadvantage is that the components are relied upon for stability, and in the long run, this may lead to problems with the fixation of the components to the bone. In addition, resection of the cruciates is believed to reduce the proprioceptive response of the knee with consequent compensatory gait patterns. A further disadvantage is that extremes of motion which occur during more demanding activities may be restricted, a possible disadvantage to younger or active patients. One approach to this problem is to use a meniscal bearing type of arrangement, already embodied in several designs, notably the LCS New Jersey, the Oxford, the Minns, and the Polyzoides—see U.S. Pat. Nos. 4,340,978 and 4,085,466. In these designs, anterior-posterior translation and internal-external rotation is completely unrestricted, except by impingement of the plastic bearing pieces onto capsular soft tissue at the anterior and posterior of the tracks. An important restriction to the designs however is that both the anterior and posterior cruciate ligaments are required, otherwise the stability is insufficient and the plastic bearings can dislocate.

At least two of the designers of the above-named devices have considered the distal-posterior radius problem of the femoral component. If the radii were different, as in FIG. 3, then the main advantage of the meniscal bearing concept, complete contact and low stresses, would be lost. U.S. Pat. No. 4,340,978 shows the meniscal bearing concept. In FIGS. 1 and 3 of this U.S. patent, the Oxford scheme is shown in U.S. Pat. No. 4,085,466. A uni-condylar femoral component has a spherical radius, but does not carry up into a patella flange. The New Jersey design opts for smaller radii posteriorly than distally (FIG. 22), and illustrates the loss of full conformity in flexion in FIG. 33.

One further improvement provided by the present invention is to provide for sufficient anterior-posterior and rotational stability so that the prosthesis can be used with or without the cruciate ligaments, and to provide complete femoral-tibial conformity throughout the entire range of flexion. In essence, it consists of making the polished metal platform for supporting the plastic bearing piece or pieces concave when seen in the sagittal view. The effect will be to offer steadily increasing resistance to displacement away from the neutral position. In this respect, the stability and laxity characteristics can be made similar to that of a normal knee, or to a usual type of condylar prosthesis. The schematic views (FIG. 7(a) shows the overall arrangement seen in plan view, with a metal plate or platform 71, for attachment to the tibia, having a polished cylindrical surface on the top of the plate and a plastic bearing component 72 which slides on the polished surface. The femoral condylar surfaces are intended to have a constant sagittal radius in the region which articulates against the plastic surface, and conform closely with the tibial surface in both frontal and sagittal planes. An important feature is that the radius of the plastic surface is smaller than that of the cylindrical surface. The cylindrical shape of the bearing surfaces is shown in FIG. 7(b) in which $R^2$ is greater than $R^1$. FIG. 7(c) shows the medial-lateral section and a central fixation peg 73 and anti-rotation pegs 74 to prevent the platform 71 rotating on the tibia.

For a one-piece plastic component of the kind shown in FIGS. 7(a)-7(c), rotation is not possible without loss of complete contact on the cylindrical surfaces. However, anterior-posterior displacement is possible. The arrangement providing anterior-posterior motion from a one-piece plastics tibial bearing component is shown in FIGS. 8(a) and 8(b) The metal platform 81 supports a plastics bearing component 82 which is guided for anterior-posterior motion on a rail 83 fixed or integral with the platform 81. The platform may be curved in the sagittal plane as shown in FIG. 7(b) or be planar. It may be convenient to constrain anterior-posterior motion within limits by providing suitable stops, e.g by means of an upstanding post 84 secured to the platform and an elongated hole 85 in the bearing pad 82. Thus, the pad 82 may move freely in an anterior-posterior direction into the post 84 abutting one of the ends of the elongated hole. An alternative method of providing stops is indicated in dotted lines in FIG. 8(a) in which the recess in the plastics meniscus component 82 has a wall 86 against which the end face of the rail 83 abuts to limit the anterior-posterior movement in one direction.

Separate plastics pads 91,92 (see FIGS. 9(a) and 9(b)) are an alternative arrangement supported on a common metal platform 93. Linear guidance is achieved by a metal rail 94, leaving a small clearance between the pads and the rail. Again, the bearing surface between the platform and the pads may be curved or planar. For two separate plastic components, both anterior-posterior translation and internal-external rotation are possible. For the latter, for bearing surfaces spaced apart 48 mm, only 0.8 mm inwards motion per side is needed to accommodate up to about $+-15$ degrees of rotation.

Different ways can be envisaged to engage the plastic components, such as by T-shaped metal rails, under which a plastic lip is captured. This is illustrated in FIG. 10, which is a view similar to FIG. 7(c). A tibial bearing pad 101 is supported for sliding anterior-posterior motion on platform 103 The pad 101 is trapped and guided by rail 102 having a 'T'-shaped profile section FIG. 10 also shows an alternative trapping and guidance means by lateral guides 104 having inwardly turned projections 105 which engage in slots in the plastics pad. A central guide rail is preferred since this is less prone to jamming.

In the construction described above the femoral components and tibial metal platform are made from a metal acceptable for use for implantation in the human body. Examples are cobalt-chromium and titanium alloys and stainless steels. The artificial patella (where present) and/or the plastics bearing components may be made from any biocompatible material capable of withstanding the imposed loads and providing appropriate bearing properties when in contact with a polished metal surface. Preferably, the plastics material should exhibit low friction properties under these conditions. Examples of suitable materials are ultra-high molecular weight polyethylene or acetal copolymers.

I claim:

1. A knee prosthesis which comprises a femoral component having at least one condylar bearing surface having an anterior portion, a posterior portion and a distalmost point therebetween, wherein the radius of the bearing surface in each sagittal section is substantially constant from posterior to a point more anterior than the distalmost point, a tibial component and a meniscal bearing component between the femoral and tibial components, said meniscal bearing component having a concave bearing surface for supporting the femoral component, the bearing surfaces in the respective sagittal sections of the femoral and meniscal bearing components being substantially continuous from posterior to anterior, whereby contact between the femoral and meniscal bearing component can be maintained across a substantial width of the condylar bearing surface throughout the range of flexion and wherein the prosthesis includes guide means for guiding the meniscal bearing component on said tibial component through sliding movement substantially constrained to an anterior-posterior axis.

2. A prosthesis according to claim 1, wherein the femoral component is shaped in said anterior portion to provide a patella groove for receiving an anatomical or artificial patella, said groove having shape which corresponds to that of a patella, whereby a patella can slide in substantial conformity with the patella through flexion of said prosthesis between 0° an 90°.

3. A prosthesis according to claim 1 or 2 wherein the tibial component comprises a metal platform having a plastics meniscal bearing component supported thereon, said metal platform having an upwardly concave surface and said meniscal bearing component having a bearing surface whose curvature substantially corresponds with the upwardly concave surface of said metal platform and wherein the curvature of said upwardly concave surface and of said bearing surface lies on a cylinder whose axis extends in a generally lateral-medial line.

4. A prosthesis as claimed in claim 3, wherein said cylinder has a radius which is at least as large as the sagittal axis of the condylar bearing surface.

5. A prosthesis according to claim 3, which includes two tibial plastics bearing components supported on said metal platform, the bearing surface of each plastics component substantially lying on a cylinder whose axis extends in a lateral-medial line.

6. A prosthesis according to claim 1, wherein the tibial component comprises a metal platform and wherein the sliding movement of the meniscal bearing component relative to the metal platform is constrained to an anterior-posterior direction by guide means on said metal platform.

7. A prosthesis according to clam 6, wherein the guide means comprises a ridge formed on the metal platform extending in the anterior-exterior direction and cooperating with the meniscal component.

8. A prosthesis according to claim 1, wherein the tibial component comprises a metal platform and a pair of meniscal plastics bearing components are located on opposite sides of a guide rail extending in an anterior-posterior direction and serving to guide said plastics bearing components for sliding movement relative to the metal platform in an anterior-posterior direction.

9. A prosthesis according to claim 8, wherein a small clearance is provide between said meniscal bearing components and the guide rail, the clearance being such as to permit limited freedom of internal-external rotation of said meniscal bearing components on said platform.

10. A prosthesis according to claim 1 wherein the tibial component comprises a metal platform and said guide means comprises a rail member attached to the metal platform and extending the anterior-posterior direction.

11. A prosthesis according to claim 10, wherein the rail member extends between lateral and medial condylar parts of the femoral component.

12. A prosthesis according to claim 10, wherein the rail member is substantially 'T'-shaped in cross-section and engages in slots provided in the meniscal bearing component whereby the rail member both guides and traps the meniscal member on the tibial component.

13. A prosthesis according to claim 10, wherein the guide means includes stops limiting the extent of sliding motion of said meniscal bearing component in an anterior or posterior direction.

14. A prosthesis according to claim 13, wherein the stops comprise a post upstanding from said rail and engaging in a slot in the meniscal bearing component.

15. A prosthesis according to claim 1, wherein the tibial component comprises a metal platform having two plastics meniscal bearing components supported thereon, each meniscal bearing component being disposed between a condylar bearing surface and said tibial platform.

16. A prosthesis according to claim 15, wherein the plastics meniscal components are located on opposite sides of guide rail extending in an anterior-posterior direction and serving to guide said plastics components for sliding movement relative to the metal platform in an anterior-posterior direction.

17. A prosthesis according to clam 16, wherein a small clearance is provided between said meniscal components and the guide rail, the clearance being such as to permit limited freedom of internal-external rotation of said meniscal bearing components on said platform.

* * * * *